US00PP11977P2

(12) United States Plant Patent
Booman

(10) Patent No.: US PP11,977 P2
(45) Date of Patent: Jul. 3, 2001

(54) BEGONIA PLANT NAMED 'ALBUQUERQUE MIDNIGHT SKY'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,775

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Albuquerque Midnight Sky', characterized by its uniform growth habit; moderate plant vigor; no requirement for winter dormancy; and interesting and attractive leaf coloration and pattern.

1 Drawing Sheet

BACKGOUND OF THE INVENTION

The present invention relates to a new and distinct cultivar of Begonia plant, botanically known as *Begonia rex* hybrid, commercially known as Rex Begonia, and hereinafter referred to by the name 'Albuquerque Midnight Sky'.

The new Rex Begonia was discovered and selected by the Inventor in a controlled environment in Vista, Calif., in 1995, within a large group of seedling progeny from multiple crossings of unidentified selections of *Begonia rex* hybrids.

The selection of this plant was based on its uniform growth habit, moderate plant vigor, salt tolerance and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Albuquerque Midnight Sky' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Albuquerque Midnight Sky'. These characteristics in combination distinguish 'Albuquerque Midnight Sky' as a new and distinct Rex Begonia:

1. Uniform growth habit.
2. Moderate plant vigor.
3. Does not require winter dormancy.
4. Interesting and attractive leaf coloration and pattern.

In side-by-side comparisons conducted by the Inventor in Vista, Calif., plants of the new Rex Begonia differ from plants of the nonpatented cultivar Merry Christmas Corkscrew in the following characteristics:

1. Plants of the new Rex Begonia are more vigorous and are bushier than plants of the cultivar Merry Christmas Corkscrew.

2. Leaves of plants of the new Rex Begonia are brighter, more purple and less green in color, and have a finely spotted pattern compared to leaves of plants of the cultivar Merry Christmas Corkscrew.
3. Leaves of plants of the new Rex Begonia do not have a "corkscrew" formation whereas leaves of plants of the cultivar Merry Christmas Corkscrew have a "corkscrew" formation.
4. Plant of the new Rex Begonia do not require a winter dormancy period whereas plants of the cultivar Merry Christmas Corkscrew do require a winter dormancy period.

In side-by-side comparisons conducted by the Inventor in Vista, Calif., plants of the new Rex Begonia differ from plants of the nonpatented cultivar Lillium in the following characteristics:

1. Plants of the new Rex Begonia are more compact than plants of the cultivar Lillium.
2. Leaves of plants of the new Rex Begonia and the cultivar Lillium differ in coloration and pattern.
3. Plants of the new Rex Begonia do not require a winter dormancy period whereas plants of the cultivar Lillium do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Albuquerque Midnight Sky'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif. under conditions which approximate commercial practice. Plants used for this description were grown in 15-cm containers for about 3 months.

Botanical classification: *Begonia rex* hybrid cultivar Albuquerque Midnight Sky.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 22.8 cm.

*Plant width.*—About 51 cm.

*Leaves.*—Arrangement: Simple. Length: Petiole to apex: About 15.2 cm. Base to apex: About 21 cm. Width: About 14.2 cm. Shape: Asymmetrical, oblique. Apex: Acute. Base: Asymmetrically cordate. Margin: Pectinate; irregularly undulate. Texture: Leathery, rugose; pubescence on lower surface veins. Color: Young foliage, upper surface: Overall metallic luster. margin: 187A, close 202A; occasional blotches of 186C. Central venal areas: 187A, close to 202A, with minute spots of 186B. Blade: 186B to 186C with satin sheen merging with iridescent 194C. Inframarginal: 147A with many spots, 194C. Young foliage, lower surface: Margin: 187A. Central venal areas: 183A to 183B. Background: Close to 148C. Mature, fully expanded, foliage, upper surface: Overall metallic luster. Margin: Dark brown, 200A. Central venal areas: 200A with many spots, 186B to 186C. Blade: Satiny sheen, 186A to 186B to 186C, merging with iridescent 194B which dissipates into spots against background, darker than 147A. Veins: 166A. Mature, fully expanded, foliage, lower surface: Margin: 200A. Blade: 183A to 181A. Background: Intervenal, 148D. Veins: 183A; reticulate.

*Petioles.*—Length: About 14.5 cm. Diameter: About 7.5 mm. Shape: Longitudinally grooved. Texture: Pubescent. Color: 166A.

*Stiplules.*—Length: About 11.5 mm. Diameter at base: About 8 mm. Shape: Deltoid. Color: 178A.

Flower description:

*Flowering habit.*—Male flowers, single with one whorl of four tepals. Female flowers, semi-double with three tepals interior to outer whorl of five tepals. Usually about three flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 2.6 cm. Depth (height): About 1.5 cm. Aspect: Drooping about 60° from vertical. Fragrance: None.

*Flower buds.*—Shape: Spherical; bulbous with marginal lip. Length: About 12.5 mm. Diameter: About 9.5 mm. Color: Close to 180C to 179B.

*Tepals.*—Arrangement: Rosette. Length: About 1.4 cm. Width: About 1.1 cm. Shape: Ovate with obtuse apex. Margin: Entire. Texture: Smooth, waxy; iridescent, translucent. Color: When opening, upper surface: 55C to 55B. When opening, lower surface: 52D. Fully opened, upper surface: 55B to 55C. Fully opened, lower surface: 52D to 55C.

*Peduncles.*—Angle: About 45° from vertical. Length: About 3.3 cm. Diameter: About 2 mm. Strength: Firm. Texture: Smooth, waxy. Color: Close to 166A.

*Pedicels.*—Angle: About 35° from vertical. Length: About 1.4 cm. Diameter: About 2 mm. Strength: Moderate. Texture: Smooth, waxy. Color: 172A.

*Reproductive organs.*—Male flowers. Stamen quantity: About 67, globose mass. Anther shape: Rhomboidal; lower sides curved inwardly. Anther length: About 2 mm. Filiament length: About 1 mm. Anther color: Close to 15A. Filament color: 41B. Pollen: Not observed. Female flowers: Pistil length: About 1.9 cm. Stigma shape: Funnel; bilobate. Stigma color: 169A. Ovary: Inferior; three-winged; one large top wing, 179A; lower wings, 171A to 172A.

Disease resistance: Resistance to diseases common to Rex Begonia has not been determined.

Seed production: Seed production has not been observed.

It is claimed:

1. A new and distinct cultivar of Rex Begonia plant named 'Albuquerque Midnight Sky', as illustrated and described.

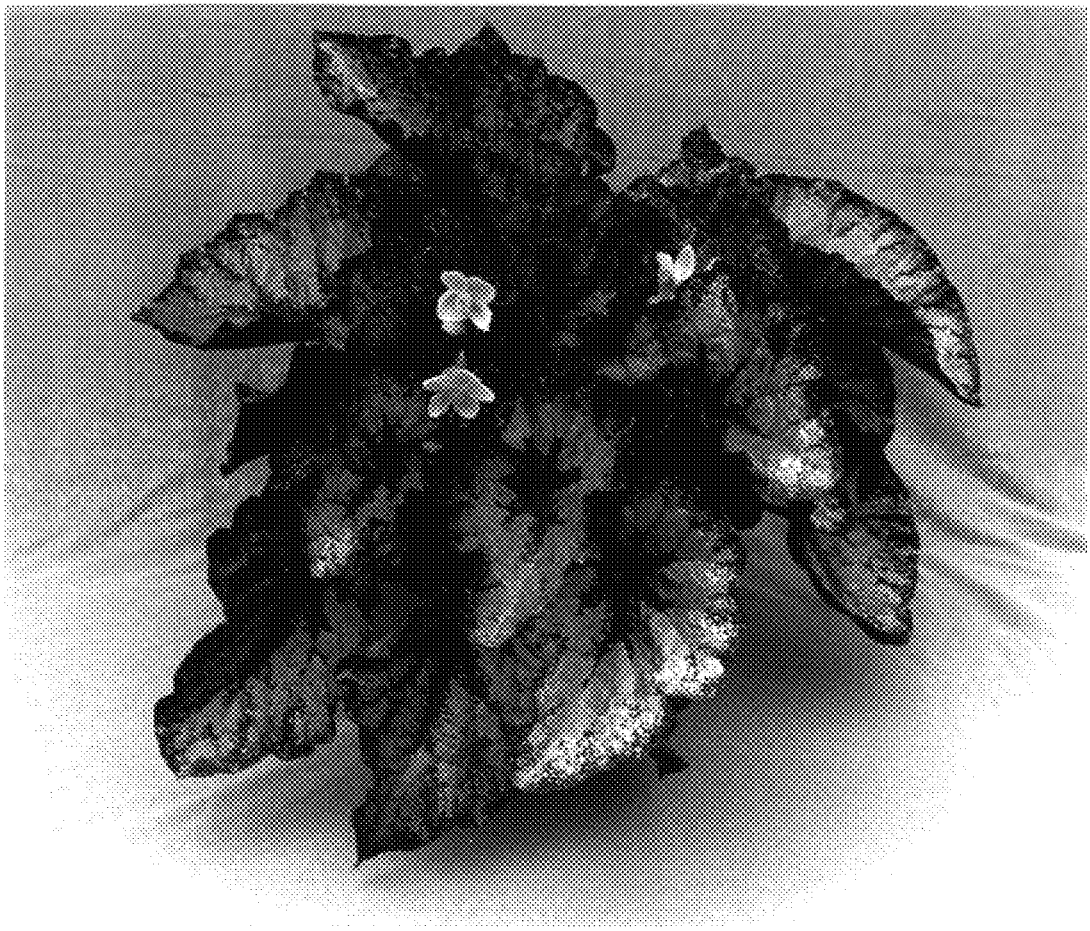

* * * * *